United States Patent [19]

Ofori

[11] Patent Number: 6,090,737
[45] Date of Patent: Jul. 18, 2000

[54] REMOVAL OF LEAD FROM ORGANIC DIARYL CARBONATE REACTION MIXTURES

[75] Inventor: John Yaw Ofori, Niskayuna, N.Y.

[73] Assignee: General Electric Company, Schenectady, N.Y.

[21] Appl. No.: 09/218,636

[22] Filed: Dec. 22, 1998

[51] Int. Cl.[7] ............................. C07C 69/96; C02F 1/72; C01G 21/02; B01J 20/34
[52] U.S. Cl. ............................ 502/20; 210/758; 210/912; 423/619
[58] Field of Search .......................... 423/619; 210/758, 210/912; 502/20; 558/274

[56] References Cited

U.S. PATENT DOCUMENTS

| | | | |
|---|---|---|---|
| 4,175,015 | 11/1979 | Mohring et al. | 204/131 |
| 4,187,242 | 2/1980 | Chalk . | |
| 4,508,688 | 4/1985 | Lorimer et al. | 423/92 |
| 5,166,393 | 11/1992 | Fukuoka et al. | 558/274 |
| 5,210,268 | 5/1993 | Fukuoka et al. | 558/270 |
| 5,231,210 | 7/1993 | Joyce et al. . | |
| 5,284,964 | 2/1994 | Pressman et al. . | |
| 5,399,734 | 3/1995 | King, Jr. et al. . | |
| 5,498,789 | 3/1996 | Takagi et al. . | |
| 5,760,272 | 6/1998 | Pressman et al. . | |
| 5,872,275 | 2/1999 | Komiya et al. | 558/270 |

*Primary Examiner*—Tom Dunn
*Assistant Examiner*—Cynthia Donley
*Attorney, Agent, or Firm*—Noreen C. Johnson; Douglas E. Stoner

[57] ABSTRACT

A method for efficient removal of lead co-catalyst species from organic process streams arising from diaryl carbonate synthesis, by contacting the organic reaction mixtures with an aqueous acid, salt, or acid/salt solution, thereby extracting the treated mixture into an aqueous phase, or by treating the organic reaction mixtures with solid oxalic acid or oxalic acid salt, or an aqueous solution of oxalic acid or oxalic acid salt, thereby resulting in precipitation of the lead. The precipitated lead may then be calcined to provide a lead compound that is catalytically active in the carbonylation of phenol to yield diary carbonates. Use of these methods will substantially reduce both financial and environmental concerns for the preparation of diaryl carbonates.

18 Claims, No Drawings

REMOVAL OF LEAD FROM ORGANIC DIARYL CARBONATE REACTION MIXTURES

BACKGROUND OF THE INVENTION

The present invention relates to a method for purification of the reaction mixtures arising from the production of diaryl carbonates. In particular, the present invention relates to removal of lead species from the process streams arising from the production of diaryl carbonates.

Diaryl carbonates, and diphenyl carbonate in particular, are valuable monomer precursors for the preparation of polycarbonates by melt transesterification. An advantageous route for the synthesis of diaryl carbonates is the direct carbonylation of aromatic hydroxy compounds by carbon monoxide and an oxidant in the presence of a catalyst.

A wide range of catalysts may be used in this preparation of diaryl carbonates. For example, U.S. Pat. No. 4,187,242 to Chalk discloses catalysts derived from Group VIIIB metals, i.e., metals selected from the group consisting of ruthenium, rhodium, palladium, osmium, iridium and platinum, or complexes thereof. U.S. Pat. No. 5,231,210 to Joyce, et al., U.S. Pat. Nos. 5,284,964 and 5,760,272 to Pressman et al., and U.S. Pat. No. 5,399,734 to King, Jr., et al. further disclose the use of co-catalysts, including metal co-catalyst species such as cobalt pentadentate complexes and complexes of cobalt with pyridines, bipyridines, terpyridines, quinolines, isoquinolines, aliphatic polyamines such as ethylenediamine, crown ethers, aromatic or aliphatic amine ethers such as cryptands, and Schiff bases, in combination with organic co-catalysts such as terpyridines and quaternary ammonium or phosphonium halides.

U.S. Pat. No. 5,498,789 to Takagi further discloses the use of a catalyst system comprising at least one lead compound soluble in a liquid phase, at least one halide selected from quaternary ammonium halides and quaternary phosphonium halides, and optionally at least one copper compound. As examples of suitable lead compounds, the publication disclosed lead oxides such as PbO, $Pb_3O_4$, $PbO_2$ and the like; inorganic lead salts such as $Pb(NO_3)_2$, $PbSO_4$ and the like and other lead compounds generally represented by the formula $Pb(OR)_2$, wherein R is an alkyl or aryl group, for example $Pb(OCH_3)_2$, $Pb(OC_6H_6)_2$; or wherein R is an acyl group, for example acid salts of lead such as $Pb(OC(O)CH_3)_2$, $Pb(OC(O)CH_3)_4$, $Pb(OC(O)C_2H5)_2$ and the like; and lead complex compounds such as phthalocyanine lead.

As can be seen from the above brief review, the crude reaction mixtures arising from the production of diaryl carbonates can contain complex mixtures of catalyst and co-catalyst metals, and organic products and by-products. The cost of commercially implementing direct oxidative carbonylation depends heavily on a combination of the efficiency of the catalyst system and on the ability to reclaim and recycle unconverted hydroxy aromatic starting material and the expensive catalyst components. Even reclamation of less expensive metals such as lead can lead to financial and environmental advantages. Accordingly, there remains a need for efficient, convenient methods for the removal of lead from the reaction mixtures generated in the carbonylation of hydroxy aromatic compounds.

SUMMARY OF THE INVENTION

The above-discussed and other drawbacks and deficiencies of the related art are alleviated by the present methods for the removal of lead species from the organic process streams of diaryl carbonate synthesis. One embodiment comprises extracting an organic reaction mixture arising from the production of diaryl carbonates with an acidic, aqueous solution comprising an anion selected from the group consisting of nitrate, halide, or acetate. A second embodiment comprises forming a lead compound which is at least partially insoluble in an organic reaction mixture arising from the production of diaryl carbonates; and separating the insoluble lead compound from the organic reaction mixture. The recovered lead-containing solid may then be calcined to provide a calcined lead compound which is catalytically active in the production of diaryl carbonates. Implementation of this method reduces both economic and environmental concerns in the preparation of diaryl carbonates.

DETAILED DESCRIPTION OF THE INVENTION

The present invention makes possible efficient removal of lead species from organic process streams resulting from the production of diaryl carbonates by catalytic carbonylation of aromatic hydroxy compounds. The process may be described generally as treating an organic reaction mixture arising from the production of diaryl carbonates so as to form a lead compound which is at least partially insoluble in the organic reaction mixture; and separating the insoluble lead compound from the organic reaction mixture. In one embodiment, the method comprises contacting the reaction mixture with an aqueous solution into which lead migrates at least partially, relative to the crude reaction mixture. Preferably, this first embodiment comprises treating an organic reaction mixture from the production of diaryl carbonates with a neutral or slightly acidic, aqueous solution of an anion selected from the group consisting of acetate, nitrate, or a halide anions, thereby extracting lead from the reaction mixture into the aqueous solution. In a second embodiment, the method comprises precipitating the lead species from an organic reaction mixture from the production of diaryl carbonates by the addition of oxalic acid, or an acidic or neutral solution of oxalic acid to the reaction mixture. The precipitated solid is then separated, and may be calcined to provide a calcined lead compound, which is catalytically active in the production of diaryl carbonates, by catalytic carbonylation of aromatic hydroxy compounds.

In accordance with the first embodiment, the lead in a crude or pre-treated organic reaction mixture arising from the production of diaryl carbonates by catalytic carbonylation of aromatic hydroxy compounds is removed by solvent extraction using a neutral or slightly acidic aqueous extractant. The pH of the aqueous solution is preferably from about 0 to about 7, more preferably from about 1 to about 4, and most preferably from about 1 to about 3. The solution further comprises at least one anion selected from the group consisting of acetate, nitrate, or halide anions. Preferred halides are chloride and bromide. Combinations of the foregoing anions may also be used. These anions result in removal of up to about 30%, and preferably up to about 50% by weight of the lead per extraction, that is, per contact of the organic reaction mixture with a single volume of extractant.

A second embodiment of the present method comprises treating a crude or pre-treated organic reaction mixture from the catalytic carbonylation of diaryl carbonates with solid oxalic acid or a solid oxalic acid salt, or with a concentrated, neutral or slightly acidic solution of oxalic acid or an oxalic acid salt. Treatment with a concentrated solution is preferred, as it allows faster dissolution of the oxalic acid or oxalic acid salt.

Treatment of the reaction mixture with oxalate results in precipitation of lead species from the reaction mixture. The precipitated lead species is typically recovered by filtration, and may be disposed of or further treated to recover the lead. In a particularly advantageous feature, calcination of the precipitated lead species under air results in production of a calcined lead compound that is catalytically active in the carbonylation of aromatic hydroxy compounds to produce diaryl carbonates. Any lead remaining in the treated organic phase may be extracted as described above with a neutral or slightly acidic, aqueous solution of an anion selected from the group consisting of acetate, nitrate, or a halide, thereby extracting lead from the treated organic phase into the aqueous solution.

Without being bound by theory, it is hypothesized that during extraction acetate, nitrate, and halide anions selectively complex with lead present in the reaction mixtures, which increases the solubility of the lead in aqueous extractant and/or decreases the solubility of lead in the organic reaction mixture. It is furthermore hypothesized that upon treatment with aqueous oxalate solutions, lead-oxalate complexes are formed, which are insoluble in the reaction mixture. Other anions may therefore be effective in either extraction or precipitation, as long as such anions are effective to extract or precipitate lead in an amount of up to about 30%, preferably up to about 50%, more preferably up to about 80%, and most preferably up to about 90% by weight of the lead per extraction or precipitation. Preferably, such anions do not extract or precipitate other metal anions or other undesired species into the aqueous extract or solid precipitate, and do not themselves pose a waste disposal problem.

The concentration of anion effective to form a lead compound which is extractable or which precipitates lead is empirically determined, and will depend on factors such as how the lead compound is formed, the nature of the anion, the concentration of the anion, the pH of the solution, and the like. In general, an effective concentration of the anion in an aqueous extraction or precipitation solution is in the range from about 0.1 percent by weight to about 20 percent by weight, and preferably in the range from about 1 percent by weight to about 10 percent by weight. A preferred aqueous extraction solution comprises between about 7 percent by weight and about 9 percent by weight of sodium acetate and between about 5 percent by weight to about 7 percent by weight of acetic acid. A preferred aqueous precipitation solution comprises between about 0.1 percent by weight and about 2 percent by weight oxalic acid or oxalate anion in the reaction mixture.

Suitable counterions for the above-mentioned anions include hydrogen, sodium, other alkali metals, alkaline earth metals, and the like. Suitable counter-ions preferably do not interfere with the extraction of lead, cause the extraction of undesirable species into the aqueous layer, or themselves present a disposal problem.

The lead-containing aqueous extract solutions obtained in accordance with the first embodiment may be disposed of, or further treated in order to isolate the lead, e.g., by selective precipitation. These precipitates, as well as the precipitates obtained in accordance with the second embodiment may then be disposed of, or further treated in order to recover the lead. Recovery of lead from a precipitate to yield a catalytically active lead compound or precursor is achieved by subjecting the precipitate to a heating program effective to regenerate lead catalyst. Accordingly, the precipitate is heated to a temperature in the range between about 400° C. and about 600° C.

The following examples are provided by way of example only, and should not be read to limit the scope of the invention.

EXAMPLE 1

7.3 g of a crude reaction mixture arising from the carbonylation of phenol and having a lead concentration of 1563 ppm was contacted with 7.6 g of 3% HCl, mixed for 3 minutes, and allowed to settle for 10 minutes. The lead content of the organic phase after extraction was 18 ppm, representing a removal efficiency of approximately 98.9%. The crude reaction mixture arose from a carbonylation using 60.5676 g (643.6 mmol) of phenol in the presence of 9.9 mg of Pd(acetylacetonate)$_2$ (0.032 mmol), 212 mg of PbO (0.950 mmol), and 3.2049 g of hexaethylguanidinium bromide (10.36 mmol) for 2.5 hours at 100° C.

EXAMPLE 2

A sample of a crude reaction mixture using a catalyst system comprising 4.6 mg (0.0151 mmol) of palladium acetylacetonate, 52.1 mg (0.2334 mmol) of lead (II) oxide and 3.2 g (10.359 mmol) of hexaethylguanidinium bromide in 60.4226 g phenol reacted for 2 hours at 100° C., and containing about 391 ppm lead, was extracted with 8.7 weight % sodium nitrate solution in an approximately a 2:1 ratio by mass of organic to aqueous components (13.7 g organic reaction mixture to 7.341 g aqueous solution). After extraction, the concentration of lead in the organic phase was 234 ppm as measured by atomic absorption. This represents a removal efficiency of 40.2 %.

EXAMPLE 3

1123.5 g of a crude reaction mixture containing 3180 ppm of lead at the end of the reaction (as determined by atomic absorption spectroscopy) was treated with an aqueous solution comprising 2.896 g of oxalic acid in 10.1 g of water. The mixture was mixed for ten minutes and then allowed to stand after mixing at 85° C. for 2 hours, then filtered to recover a cake (8.21 g). The filtrate was analyzed for lead by atomic adsorption spectroscopy, which showed a lead content of 12.5 ppm. This represents a removal efficiency of 99.6% for the lead.

COMPARATIVE EXAMPLE 4

627.1 g of the crude reaction mixture from the same source as in Example 3 was filtered and the filtrate analyzed by atomic absorption spectroscopy, which showed that the filtrate contained 2625 ppm of lead (compared to the initial lead concentration of 3180 ppm). The filter cake collected weighed 3.917 g.(There was no oxalic acid or water added, for comparison). This was intended only as a comparison to the previous case, which started with 1123.5 g.

EXAMPLE 5

377 mg of the filtered solid obtained in Example 3 was subjected to a heating program, wherein the sample was heated under air. The temperature was increased from room temperature to 600° C., at a rate of 20° C. per minute, and then held at 600° C. for 15 minutes (total time of heating of about 45 minutes). The loss in weight of the sample was 28%, and had reached that weight loss after about 20 minutes (about 450° C.).

The solid recovered was used as a lead co-catalyst in a catalytic carbonylation of phenol (61.2543 g phenol, 5.5 mg of palladium acetylacetonate, 103.2 mg of the solid recovered from the heat treatment described above, and 2.1711 g tetraethylammonium bromide). The reaction yielded 14.8% of diphenyl carbonate in 1.5 hours, clearly showing the catalytic activity of the lead-containing solid. By comparison, without any lead species present, less than 1% of diphenyl carbonate is obtained.

EXAMPLE 6

Four successive extractions of an organic diphenylcarbonate reaction mixture were performed at 80° C., using a sodium acetate/acetic acid aqueous solution (7.22% sodium acetate, 5.26% acetic acid by weight). Results are shown in Table 1 below.

TABLE 1

| Extraction No. | Organic solution, g | Aqueous solution, g | Initial lead in organic, ppm | Final lead in organic, ppm | Lead in aqueous extractant, ppm |
|---|---|---|---|---|---|
| 1 | 10 | 10 | 1846 | 775 | 1130 |
| 2 | 11.6 | 10 | 775 | 355 | 470 |
| 3 | 8.9 | 10 | 355 | 153 | 180 |
| 4 | 5.8 | 6 | 153 | 78 | 50 |

The data in Table 1 show that the estimated removal efficiency of lead from the organic phase per contact is around 55%, leading to a removal of in excess of 90% with four extractions.

EXAMPLE 7

The data in Table 2 below shows the results of three successive extractions of a crude reaction mixture at 80° C., using the same sodium acetate/acetic acid solution as in Example 6. Again, the estimated removal efficiency per contact was around 55%, with the overall effectiveness from three contacts exceeding 90%.

TABLE 2

| Extraction No. | Organic solution, g | Aqueous solution, g | Initial lead in organic, ppm | Final lead in organic, ppm | Lead in aqueous extractant, ppm |
|---|---|---|---|---|---|
| 1 | 10 | 10 | 4269 | 1872 | 2750 |
| 2 | 11.7 | 10 | 1872 | 892 | 1090 |
| 3 | 9.5 | 10 | 891 | 371 | 440 |

While preferred embodiments have been shown and described, various modifications and substitutions may be made thereto without departing from the spirit and scope of the invention. Accordingly, it is to be understood that the present invention has been described by way of illustration and not limitation.

I claim:

1. A method of removing lead from an organic reaction mixture arising from the production of diaryl carbonates comprising forming a lead-containing compound which is at least partially insoluble in an organic reaction mixture arising from the production of diaryl carbonates; and separating the lead-containing compound from the organic reaction mixture.

2. The method of claim 1, wherein forming the at least partially insoluble lead-containing compound is by treating the organic reaction mixture with a reagent selected from the group consisting of solid oxalic acid, a solid oxalic acid salt, an aqueous solution of oxalic acid, an aqueous solution of an oxalic acid salt, and a combination thereof.

3. The method of claim 2, wherein the amount of oxalic acid or oxalic acid salt is about 0.1% by weight to about 2% by weight of the reaction mixture.

4. The method of claim 2, wherein the reagent is solid oxalic acid.

5. The method of claim 1, further comprising treating the separated, lead-containing compound to yield a catalytically active lead compound or precursor to a catalytically active lead compound.

6. The method of claim 5, wherein the treating is by heating the lead-containing compound to a temperature between about 400° C. and about 600° C.

7. The method of claim 6, wherein the treating is under air.

8. The method of claim 1, further comprising extracting lead from the organic reaction mixture after separation of the lead-containing compound with a neutral or acidic aqueous solution comprising an anion selected from the group consisting of acetate anion, nitrate anion, halide anion, and mixtures thereof.

9. A method of removing lead from an organic reaction mixture arising from the production of diaryl carbonates comprising treating the organic reaction mixture with a reagent selected from the group consisting of solid oxalic acid, a solid oxalic acid salt, an aqueous solution of oxalic acid, an aqueous solution of an oxalic acid salt, and a combination thereof, thereby forming an at least partially insoluble lead-containing compound;

separating the lead-containing compound from the organic reaction mixture; and calcining the separated, lead-containing compound to yield a catalytically active lead compound or precursor to a catalytically active lead compound.

10. A method of removing lead from an organic reaction mixture arising from the production of diaryl carbonates comprising contacting an organic reaction mixture arising from the production of diaryl carbonates with a neutral or acidic aqueous solution comprising an anion which forms a water-soluble salt with lead, thereby extracting lead into the aqueous solution.

11. The method of claim 10, wherein the anion is selected from the group consisting of acetate anion, nitrate anion, halide anion, and mixtures thereof.

12. The method of claim 10, wherein the pH of the aqueous solution is in the range from about 0 to about 7.

13. The method of claim 10, wherein the pH of the aqueous solution is in the range from about 1 to about 4.

14. The method of claim 10, wherein the pH of the aqueous solution is in the range from about 1 to about 3.

15. The method of claim 10, wherein at least about 30% of the lead is removed per extraction.

16. The method of claim 15, wherein at least about 50% of the lead is removed per extraction.

17. The method of claim 10, further comprising treating the aqueous solution with extracted lead to yield a lead-containing precipitate.

18. A method of reclaiming lead from an organic reaction mixture arising from the production of diaryl carbonates comprising contacting an organic reaction mixture arising from the production of diaryl carbonates with a neutral or acidic aqueous solution selected from the group consisting of acetate anion, nitrate anion, halide anion, and mixtures thereof, thereby extracting lead into the aqueous solution.

* * * * *